United States Patent [19]
Maccone et al.

[11] 4,404,185
[45] Sep. 13, 1983

[54] SLOW RELEASE FORMULATIONS OF PHEROMONES CONSISTING OF ALDEHYDES

[75] Inventors: Sergio Maccone; Anacleto Dal Moro, both of Milan; Mario Pirozzi, S. Donato Milanese; Amedeo Capizzi, Milan, all of Italy

[73] Assignee: Montedison S.p.A., Milan, Italy

[21] Appl. No.: 375,549

[22] Filed: May 6, 1982

[30] Foreign Application Priority Data

May 7, 1981 [IT] Italy ............................... 21551 A/81

[51] Int. Cl.³ ..................... A01N 25/00; C07C 143/02
[52] U.S. Cl. .................................... 424/84; 260/513 B
[58] Field of Search ...................... 424/84; 260/513 B

[56] References Cited
U.S. PATENT DOCUMENTS
3,969,399  7/1976  Passal .............................. 260/513 B

*Primary Examiner*—Alan Siegel

[57] ABSTRACT

A slow release formulation of sex pheromones of insects consisting of aldehydes, is herein described.

The formulation consists of the bisulphite adduct of the aldehyde and a buffer having a pH value in the range from 2 to 10.

The formulations herein described are employable for attracting and catching the insects in traps or for permeating the air in an infested area, in this way disturbing and preventing copulation.

14 Claims, No Drawings

SLOW RELEASE FORMULATIONS OF PHEROMONES CONSISTING OF ALDEHYDES

BACKGROUND OF THE INVENTION

Pheromones have become, in recent years, more important in the search for methods of control of pests causing damages to agricultural cultivations. As compared with conventional agents, they have the advantage of an outstanding selectivity for one species only, or for a restricted number of closely related species, without affecting other pest species. It is, therefore, possible to combat a certain pest with the aid of pheromones, without disturbing the ecological equilibrium more than necessary.

Pheromones are secreted outside the insect body and, depending on the type of the reaction they induce, may be divided into aggregating, tracing, sex, alerting pheromones, or others.

The most broadly diffused and most interesting ones due to the applicative possibilities in the control of insect species are the sex pheromones which are secreted more frequently by females (but also by males) and attract the individuals of the opposite sex for copulation.

The natural pheromone mixture is volatile and diffuses in the air also to great distances.

When the pheromone mixture comes in contact with particular sense organs of the males (the chemoreceptive sensilla prevailingly located on the antennae), it attracts them towards the source.

If the pheromone mixture, prepared for example by synthesis, or a mixture endowed with the same effect, is available, it is possible to prepare traps containing the attracting mixture in a suitable formulation capable of ensuring a controlled release thereof. The males of a species, when coming into contact with the mixture spread in the air, are attracted towards the traps, where they are caught or killed.

The utilization of the aforesaid traps permits to carry out massive catches of males of a species, thus drastically reducing the number of copulations and, consequently, the future population of such insect species.

Another useful use of the traps containing sex attractants is that of promoting the monitoring action. In fact, by detecting the number of caught insects in the traps containing the attracting mixture and properly placed in a probably infested area, it is possible to determine with a sufficient exactness the limit of the infested area and the density of population of the insects in such area.

These data enable to intervene, if necessary and where necessary, with the conventional insecticides.

The monitoring action allows therefore to reduce the number of treatments to those strictly necessary and to limit them to the area where the infestation is present, thus attaining obvious economic and environmental advantages and avoiding at the same time the development of insect strains resistant to the insecticide utilized.

Another useful application of an insect sex attracting mixture consists in permeating an infested area with the attracting mixture, during the copulation period. As a consequence thereof, the males of the species are no longer able to distinguish the location of the females and in this way the number of copulations decreases, thus drastically reducing the future population of such insect species in the area.

In all the above-mentioned applications, the main problem to overcome, in a practical utilization, is that of achieving a sufficiently prolonged and constant release of the pheromone in the atmosphere. Since generally the copulation period, which differs from species to species, varies within certain time limits as a function of several not quantifiable environmental and climatic factors, the pheromone mixture introduced by man needs to be present in the air for a time-period sufficiently long as to surely include the short time-period during which copulation of the considered insect species occurs.

The natural pheromones whose composition has been determined contain one or more chemical compounds which may belong to different classes such as, e.g., saturated or unsaturated hydrocarbons, saturated or unsaturated high molecular-weight alcohols, acetates of the aforesaid alcohols, lower esters of fatty acids, aldehydes, ketones, etc.

For a certain number of insect species there are now available formulations of synthetic pheromone mixtures or of substances endowed with an analogous effect, which are employable in agriculture according to the methods illustrated hereinabove.

The problem connected with the slow release has been now rather successfully solved by suitable formulations or by the use of technical devices such as microencapsulation, the use of hollow capillary fibres of polymeric material or of glass, closed at one end, or the incorporation into polymeric matrices.

For the pheromones consisting of (or containing) aldehydes, the problem of the slow release has not yet been conveniently solved, since the aldehyde functional group is highly oxidizable in the presence of sunlight and air. For this reason it is difficult to directly use aldehyde pheromones with efficacious results, for example in traps, because such pheromones oxidize in a short time and are no longer effective in attracting the insects.

The other methods of fight based on the use of aldehyde pheromones present analogous problems.

Some of the most important insect species whose natural pheromone contains aldehydes are indicated in following Table 1.

TABLE I

Insect species in the natural pheromone of which aldehydes are contained.

| Insect species | Aldehydes in the pheromone |
|---|---|
| Choristoneura fumiferana | (E)-11-tetradecenal |
| Galleria mellenella | undecanal |
| Heliothis armigera | (Z)-11-hexadecenal + others |
| Heliothis virescens | (Z)-11-hexadecenal |
|  | (Z)-9-tetradecenal |
| Heliothis zea | (Z)-11-hexadecenal |
|  | (Z)-9-hexadecenal |
|  | (Z)-7-hexadecenal + others |
| Prays citri | (Z)-7-hexadecenal |
| Eustrotia candidula | (Z)-9-hexedecanal |

As is known, aldehydes form adducts with sodium bisulphite and these adducts regenerate aldehyde by treatment with acids or bases

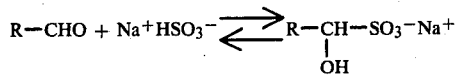

This reaction is used to purify an aldehyde since the bisulphite adducts are often in the crystalline form and can be isolated. By successive treatment with acids or bases the bisulphite ion in equilibrium with the adduct is destroyed, thus obtaining a quick regeneration of the aldehyde.

THE PRESENT INVENTION

We have now found that the aldehydes contained in the insect pheromone are suited to form adducts with bisulphite and that it is possible to have a continuous source of aldehyde by treating the corresponding bisulphite adducts with buffer solutions. We have also found that the release rate of the aldehyde pheromone can be regulated by properly choosing the pH of the buffer solution, and that buffer solutions having a pH of from 2 to 10 permit to achieve a suitable release which ensures a continuous source of aldehyde pheromone over a sufficiently long period of time. This allows to employ aldehyde pheromones in the usual fight methods in which the pheromones are used, the drawbacks arising from the easy oxidability of the aldehyde pheromones being so overcome.

Thus, it is an object of the present invention to provide a controlled and slow release formulation of aldehyde pheromones consisting of the corresponding bisulphite adduct in the presence of a buffer solution at a pH ranging from 2 to 10.

It is another object of this invention to provide a method of fighting the insects whose pheromone consists of aldehydes, such method consisting in attracting the males of a species to a pheromone source consisting of the bisulphite adduct of the aldehyde and of a buffer solution having a pH ranging from 2 to 10.

Still another object of the present invention consists in providing traps for insects whose pheromone consists of aldehydes, charged with the bisulphite adduct of the aldehyde and a buffer solution at a pH ranging from 2 to 10.

It is a further object of this invention to provide a method of disturbing and avoiding the copulation of insects whose pheromone consists of aldehydes, such method consisting in permeating the air of the infested area with the pheromone released by the bisulphite adduct of the aldehyde in the presence of a buffer solution having a pH ranging from 2 to 10.

Generally it is sufficient to use buffer solutions with a pH ranging from 3.5 to 8, because in such range the aldehyde release rate is suited to the practical uses of those aldehydes which are more frequently components of pheromone mixtures.

Among the aldehydes forming or being components of pheromone mixtures, the compound (Z)-11-hexadecenal of formula:

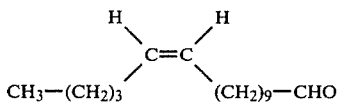

appears particularly representative.

The abovesaid aldehyde is, in fact, the basic component of the pheromone of an important pest of the cotton plants (*Heliothis armigera*), and it is a component of the pheromone mixture of other noctuid Lepidoptera (*Heliothis virescens, Heliothis zea*).

Furthermore, other pheromones of important insects are homologous or isomers of said aldehyde (see Table 1).

(Z)-11-hexadecenal exhibits the same drawbacks of the other aldehydes as regards the practical application in agriculture.

The preparation of the bisulphite adduct has proved to be an excellent method for protecting the aldehyde pheromone since the latter, in the form of adduct, exhibits a remarkably higher stability both to heat and to U.V. light (see Examples 3 and 4).

In addition, the release of the aldehyde from the bisulphite adduct by treatment with a buffer solution can be controlled for selected periods of time by the buffer pH and can be delayed over a suitably long period of time, thus meeting the requirements of a practical utilization of the pheromone in the fight against pests.

As an example, by treating the bisulphite adduct of compound (Z)-11-hexadecenal with a buffer solution at a pH=3.7, after twenty days only about 10% of the theoretical aldehyde was released, while with a buffer solution at a pH=7, about 75% of the theoretical aldehyde was released in twenty days (see Example 5).

These data show the high versatility of the formulation according to the present invention, which permits to regulate over a wide range both time and amount of release of the aldehyde, thus offering the actual possibility of using aldehyde-based pheromones in agriculture.

In some cases, to attract the insect into a trap or for similar methods of fight, it is necessary to use a mixture of aldehydes as attractant.

In such case it is sufficient to separately prepare the bisulphite adducts of the aldehydes and then to mix the adducts in proper ratios, adding then the buffer solution having the selected pH.

The synthesis of the bisulphite adducts of the aldehyde pheromones is accomplished according to the conventional techniques used for this type of reaction.

For example, it is possible to directly react the aldehyde with an aqueous solution saturated with sodium bisulphite ($NaHSO_3$) or with metabisulphite ($Na_2S_2O_5$). After a short time, even at room temperature, the adduct precipitates and may be separated by simple filtration.

The formulations, or compositions, object of the present invention are obtained, in a simple way, by suspending the bisulphite adduct in a buffer solution having the selected pH. Since the bisulphite adduct may be present also as in part unsolubilized product, it is not necessary to add additives suited to maintain the adduct in suspension.

It may be advisable to finely grind the adduct or to mash it just before adding it to the buffer solution.

The buffer solutions usable in the compositions are those commonly used, which exhibit a pH comprised in the ranges of the invention, and whose components are chemically consistent with the bisulphite adduct and the aldehyde.

As an example, a list of buffer solutions is indicated in "Handbook of Chemistry and Physics" section D, page 79, 47th edition, published by "The Chemical Rubber Co."—Cleveland, Ohio.

In the compositions forming the object of the present invention the buffer solution may be present in amounts of from 5 to 50 times by weight in respect to the bisulphite adduct, preferably of about 10 times.

For the use in agriculture the formulations object of this invention are suited to various practical solutions depending on the type of pheromone fight to be carried out. To attract the insects into traps, either for monitoring or for massive captures, it is necessary to place the formulation into the trap in a suitable container. Very useful to this purpose have proved the hollow cylindrical polyethylene phials, having a capacity of about 1 ml and equipped with a cover made of polyethylene too.

Such polyethylene phials are already utilized as dispensers of various types of pheromones due to the fact that the pheromone can diffuse through the polymeric wall and be released to the exterior.

The use of the aldehyde-based pheromones as such in said dispensers provides rather poor practical results, as the aldehyde oxidizes in a short time.

On the contrary, with the formulations of this invention it is possible to use such type of dispensers because the bisulphite adduct is much less sensible than aldehyde to the oxidizing action and the system is a continuous source of aldehyde which, by diffusing through polyethylene, is released to the environment.

In practice, the polyethylene dispenser is filled with the necessary amount of bisulphite adduct in suspension in the buffer solution. The dispenser is then closed and placed in the interior of the trap.

The traps which can be used are the ones commonly used for the capture of insects by means of pheromones.

To use the formulations of the invention in the pheromone-based fight method consisting in permeating the air in the infested area with the pheromone, in order to prevent the insect males from localizing the females, several practical solutions are possible, the choice of which depending on various factors, such as climatic conditions, type of cultivation, available distributing devices, extension of the area to be treated, and so on.

A useful solution consists in placing in the area to be treated an adequate number of pheromone sources consisting of the formulations of the invention in proper containers. Such containers may be also the polyethylene dispensers previously described.

A more capillary distribution can be attained by spraying the vegetation with aqueous suspensions of the formulations of this invention. To this purpose it is possible to prepare compositions in wettable powder of the bisulphite adduct to be suspended in water containing the buffer solution.

The compositions, or formulations, in the form of wettable powder consist of the bisulphite adduct, of a solid inert carrier and of other additives, such as surfactants, U.V. stabilizers and antioxidants (see Example 8).

The presence of antioxidants and of U.V. stabilizers becomes necessary mainly in relation to the necessity of protecting other oxidizable functional groups which are present in the molecule, such as for example olefinic double bonds.

The direct contact of the compositions of the invention with the vegetation does not cause damages to the cultivations as the compositions herein described are not phytotoxic (see Example 7).

The amount of formulation to be utilized in the different methods of use varies as a function of different factors, some of which connected with the insect species to be fought and with the type of aldehyde pheromone to be released to the environment, others connected with the fight method (massive captures, disturb of copulation), or with the monitoring action, while still others are connected with external factors such as the type of vegetation existing in the area to be treated, atmospheric conditions, etc.

In the traps it is generally possible to use composition amounts corresponding to 1-20 mg of pheromone per trap.

In order to disturb copulation, amounts of composition corresponding to 2.5-30 g of pheromone/ha may be distributed.

With a view to better illustrating the present invention, the following examples are now given.

EXAMPLE 1

Preparation of the bisulphite adduct of (Z)-11-hexadecenal

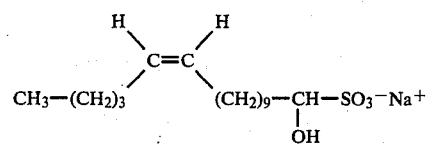

0.9 g ($3.78 \cdot 10^{-3}$ mols) of (Z)-11-hexadecenal and 2.25 ml of a saturated solution of $Na_2S_2O_5$ were charged into a 10 ml flask equipped with a magnetic stirrer.

The mixture was stirred at room temperatura and in a very short time an insoluble compound of wax-like consistency formed. It was further stirred for about 1 hour, thereupon it was filtered and the solid was washed with a few milliliters distilled water and successively with ethyl alcohol and diethyl ether.

1.3 g of the bisulphite adduct with a practically quantitative yield were obtained.

On infrared analysis the adduct shows the presence of a broad absorption band between 3,600 and 3,200 $cm^{-1}$ relating to the associated OH group, bands at 2,710 and 1,730 $cm^{-1}$ relating to the CHO group of the starting aldehyde being not present.

EXAMPLE 2

Regeneration of the aldehyde from the bisulphite adduct

The object of the present example is that of illustrating the immediate release of the aldehyde by treating the bisulphite adduct with aqueous solutions having a pH beyond the range according to the invention.

Since the percentage of aldehyde recovered by this method is very high, the procedure described hereinafter was adopted for analytical purposes in some of the following examples.

0.5 g of bisulphite adduct of (Z)-11-hexadecenal (obtained as described in Example 1), having a theoretical content of aldehyde equal to 0.345 g, were treated in a flask with 12.5 ml of a solution at 10% of $Na_2CO_3$ in distilled water (pH=12) in the presence of 20 ml of n.hexane. It was intensely stirred for about 30-60 minutes until disappearance of the wax-like adduct.

The organic phase was separated. The aqueous phase was further extracted with n.hexane (2×5 ml).

The joined organic extracts were dried on anhydrous $CaCl_2$. By removal of the solvent at reduced pressure there were obtained 0.327 g of (Z)-11-hexadecenal corresponding to about 95% of the theoretical content of aldehyde in the starting bisulphite adduct. The gas-chromatographic analysis of the solution in n.hexane and of the isolated product confirmed the recovery data and evidenced the absence of any other products.

EXAMPLE 3

Thermal stability of the bisulphite adduct

Into each of a set of dark-glass containers having a capacity of 2.5 ml there were introduced 0.35 g of (Z)-11-hexadecenal. Into another set of containers there were put 0.5 g of bisulphite adduct of (Z)-11-hexadecenal corresponding to 0.345 g of theoretical aldehyde.

The containers were accurately closed and kept in a thermostated room at 40° C.

At prefixed intervals of time a few containers were taken from each set.

The bisulphite adduct was treated according to the modalities described in Example 2.

The gas-chromatographic analysis was employed to determine the amount of residual aldehyde in the two types of samples.

The results recorded on following Table 2 show how the aldehyde pheromone in the form of bisulphite adduct exhibited a higher stability to heat.

TABLE 2

Thermal stability of (Z)-11-hexadecanal and of the bisulphite adduct at 40° C.

| Starting compound | Residual aldehyde[1] after | |
|---|---|---|
| | 7 days | 14 days |
| (Z)-11-hexadecenal at 100% | 80.3% | 57.6% |
| Corresponding bisulphite adduct | 90.2%[2] | 80.0%[3] |

Notes to Table 2:
[1] Each datum is the average of the results of 3 tests.
[2] The correct value, considering a 95% recovery of aldehyde from the bisulphite adduct according to the operative modalities of Example 2, results to be 94.9%.
[3] The correct value is 84.2%.

EXAMPLE 4

Stability of (Z)-11-hexadecenal and of the bisulphite adduct to U.V. light 100 mg of pure aldehyde were placed into a set of Petri capsules having a 3-cm diameter, while 145 mg of the bisulphite adduct corresponding to about 100 mg of theoretical aldehyde were placed into another set.

The capsules were then exposed to the radiations of a mercury-vapor lamp with λ from 320 to 400 nm and a temperature of 38° C. At prefixed times some capsules containing the aldehyde were taken out and the aldehyde was dissolved in n.hexane, and some capsules containing the bisulphite adduct were taken out and the content was treated according to the modalities of Example 2 in order to restore the aldehyde.

The content of free aldehyde or of restored aldehyde was quantitatively determined by gaschromatography.

The results recorded on following Table 3 show how the bisulphite adduct protects the aldehyde pheromone which otherwise would quickly degrade in the presence of U.V. light.

TABLE 3

Degradation of (Z)-11-hexadecenal and of the bisulphite adduct due to exposure to U.V. light.

| Starting compound | [1]Residual aldehyde after exposure for | | | | | |
|---|---|---|---|---|---|---|
| | 4 h. | 21 h. | 24 h. | 48 h. | 73.5 h. | 189 h. |
| (Z)-11-hexadecenal at 100% | 49.9% | 39.9% | — | 20.6% | 18.1% | — |
| Corresponding bisulphite adduct | — | — | 95.2% | — | 92.% | 82.9% |

Note to Table 3:
[1] Each datum is the average of the results of 3 tests.

EXAMPLE 5

Regeneration of (Z)-11-hexadecenal aldehyde from the bisulphite adduct as a function of the pH of the buffer solution A set of flasks were prepared containing a three-phase system consisting of 1 g of bisulphite adduct of (Z)-11-hexadecenal (corresponding to 0.69 g of theoretical aldehyde) at the bottom of the flask, of 100 g of a buffer solution having a prefixed pH and of 100 g of an organic solution composed of:

49 g of xylene
49 g of n.hexane
1 g of pentaerythrite 2,6-di-tert.butylphenol propionate (antioxidant)
1 g of 2-hydroxy-4-octyloxy-benzophenone (stabilizer to U.V. light).

The addition of the antioxidant and of the U.V. stabilizer to the organic phase has the scope to protect the aldehyde released by the adduct and extracted by the organic solvent.

For the tests, buffer solutions having the following pH were employed:

3.7 (sodium acetate/acetic acid)
5.0 (sodium acetate/acetic acid)
7.0 (monopotassium phosphate/sodium hydroxide).

Each sample so prepared was then kept sheltered from the light at a constant temperature of 30° C.

At certain intervals of time, 10 ml of organic phase were drawn from the flasks and were subjected to gas-chromatographic analysis in order to determine the amount of aldehyde released from the adduct.

To evaluate the aldehyde degradation, if any, in the organic phase, a diphase system was prepared which consisted of 100 g of a buffer solution with a pH=7 and of 100 g of an organic solution like the one tested in the above experiment, in which 0.69 g of pure aldehyde were dissolved.

Also this sample was kept under the same conditions as the system being tested and was periodically analyzed to determine the aldehyde degradation degree.

The results of the tests are recorded on following Table 4.

TABLE 4

| Test No. | pH of the buffer solution | Percentage of released aldehyde[1] after hours | | | | | | | |
|---|---|---|---|---|---|---|---|---|---|
| | | 0 | 24 | 72 | 94 | 216 | 336 | 456 | 480 |
| 1 | 3.7 | 0 | — | 4.5 | — | 8.58 | 9.73 | — | 11.24 |
| 2 | 5 | 0 | 3.26 | — | 6.32 | 10.5 | — | 12.0 | — |
| 3 | 7[2] | 0 | — | 32.0 (32.9) | — | 50.5 (56.8) | 50.6 (64.4) | — | 49.35 (77.2) |
| 4 | Aldehyde degradation | | | | | | | | |

TABLE 4-continued

| Test No. | pH of the buffer solution | Percentage of released aldehyde[1] after hours | | | | | | |
|---|---|---|---|---|---|---|---|---|
| | | 0 | 24 | 72 | 94 | 216 | 336 | 456 | 480 |
| | at pH = 7 | 100 | — | 97.3 | — | 88.9 | 78.7 | — | 63.9 |
| 5[3] | 12 | 0 | 100 | — | — | — | — | — | — |
| 6[3] | 0 | 0 | 100 | — | — | — | — | — | — |

Notes to Table 4:
[1]Each datum recorded is the average of at least 2 tests.
[2]The data indicated between brackets were corrected as a function of the aldehyde degradation (test No. 4).
[3]Comparative tests at pH values falling beyond the ranges according to the invention.

From the data recorded on Table 4 it is apparent that the system according to the invention allows a gradual and sufficiently slow release of the pheromones by the bisulphite adduct (tests Nos. 1, 2 and 3). Beyond the limits of the buffer pH, the aldehyde is released from the bisulphite adduct at a too high rate which is not suited to the practical purposes to be attained (tests Nos. 5 and 6).

EXAMPLE 6

Recovery test of the aldehyde pheromone in polyethylene dispensers

A set of polyethylene phials about 2 cm long, with an inside diameter of about 0.5 cm, a capacity of about 1 ml, equipped with a proper polyethylene plug, was charged with 17 mg of bisulphite adduct of (Z)-11-hexadecenal aldehyde (corresponding to 12 mg of theoretical aldehyde) and with 0.5 ml of a buffer solution at a pH=7.

An analogous set of phials was charged with 12 mg of (Z)-11-hexadecenal which was directly absorbed in the polyethylene walls. The phials were then kept in a cell thermostated at 30° C., photoperiod=15 hours, air change=160 m³/h.

A few phials were taken from the two sets at regular intervals of time. The ones containing the buffer solution were emptied.

The phials were then separately extracted with n.hexane for 24 hours in order to check the presence of pheromone in their walls.

The solution in n.hexane was subjected to gas-chromatographic analysis, so quantitatively determining the aldehyde present therein.

It is of importance to notice that the polyethylene phials were those usually utilized in traps for the catch of insects. The phials are usually charged with the pheromone and take advantage of the diffusion of the pheromone through the polyethylene walls in order to get a slow release to the environment. The results of the test are recorded on following Table 5.

Since the (Z)-11-hexadecenal content in the dispenser's polyethylene walls depends on various factors such as forming rate of aldehyde from the bisulphite adduct as a function of the selected pH, diffusion rate of aldehyde in the polyethylene walls and degradation rate of aldehyde under the test conditions, the data recorded on Table 5 are to be evaluated from a relative viewpoint.

One may conclude that, under the conditions of the test, which simulate the practical applications in traps as regards both the type of dispenser and the test parameters, the dispensers charged only with aldehyde tend to exhaust in practice their function after about 18 days (430 hours), while the dispensers charged with the bisulphite adduct and the buffer solution at a pH=7 are still capable of releasing about 20% of the theoretical aldehyde after 40 days (962 hours).

EXAMPLE 7

Determination of the phytotoxicity of the formulations of the invention

Some cotton plants about 2-month old, cultivated in a glasshouse, were sprayed till dripping with the following solutions or dispersions:
(A) Bisulphite adduct of (Z)-11-hexadecenal aldehyde in an aqueous dispersion at a 0.05% concentration.
(B) Bisulphite adduct of (Z)-11-hexadecenal aldehyde in an aqueous dispersion at a 0.25% concentration.
(C) Aqueous buffer solution at a pH=7 ($KH_2PO_4$/NaOH) at a 2% concentration.
(D) Aqueous buffer solution at a pH=7 ($KH_2PO_4$/NaOH) at a 10% concentration.

The cotton plants were then kept in a glasshouse at 18°–25° C., photoperiod=16 hours, luminous intensity=1500 lux. Eight days after the treatment no symptom of phytotoxicity was observed.

EXAMPLE 8

Restoration of (Z)-11-hexadecenal from the bisulphite adduct in contact with the vegetation The test simulated the application of the composition according to the invention in the method of pheromone

TABLE 5

(Z)-11-hexadecenal present in the polyethylene walls of pheromone dispensers.

| Starting compound | Starting amount (mg) | Aldehyde amount[1] (in mg) found after hours | | | | | | |
|---|---|---|---|---|---|---|---|---|
| | | 0 | 96 | 170 | 242 | 430 | 650 | 962 |
| Bisulphite adduct and buffer solution at pH = 7 | 17 mg (12 mg of theoretical aldehyde) | 0 | — | 6.56 | 4.5 | 2.9 | 2.6 | 2.3 |
| (Z)-11-hexadecenal | 12 mg | 12 | 8/3 | 4.3 | 1.8 | 0.5 | — | — |

Note to Table 5:
[1]Each datum recorded hereinabove is the average of 3 tests.

fight consisting in permeating the air with the pheromone in the copulation period, in a infested area.

A wettable powder having the following composition was prepared:
- 8.4 g of bisulphite adduct of (Z)-11-hexadecenal (corresponding to 5 g of theoretical aldehyde),
- 66.6 g of fossil meal (inert),
- 5.0 g of pentaerythrite 2,6-di-tert.butylphenol propionate (antioxidant),
- 5.0 g of 2-hydroxy-4-octyloxy-benzophenone (U.V. stabilizer),
- 10 g of sodium polymetacrylate (suspending agent, adhesivating agent),
- 5 g of sodium lignosulphonate (dispersant).

The bisulphite adduct was finely dispersed in about 20 ml of $CH_2Cl_2$ containing the antioxidant and the U.V. stabilizer. The mixture was sprayed onto the fossil meal and the solvent was evaporated. The other ingredients were then added and the whole was homogenized by gently grinding in a mechanical mill. An aqueous suspension containing 0.2% by weight of wettable powder and 2% by weight of buffer solution at pH=7 was then prepared.

Such suspension was utilized to spray about 2-month old cotton plants cultivated in pot. The plants were then kept in a glasshouse under the following conditions: temperature=18°-25° C., photoperiod=16 hours, luminous intensity=1500 lux, watering at regular intervals.

At the prefixed times a few plants were taken from the pots, cut into small pieces and put into a solution at 10% oF $Na_2CO_3$. The aqueous solution was then extracted with n.hexane and the organic solution was subjected to gaschromatographic analysis to determine the presence of aldehyde.

The presence of aldehyde in the extract was noticed for at least 20 days after the treatment.

It is important to notice that in the glasshouse where the plants were kept it was possible to smell, for the duration of the test, the typical odour of (Z)-11-hexadecenal released by the bisulphite adduct.

EXAMPLE 9

Field test against Eustrotia candidula

E. candidula is quite diffused in Italy and is a pest of orchards. Its sexual pheromone consists of (Z)-9-hexadecenal.

A test was carried out in a peach-orchard naturally infested by this insect in order to compare the effectiveness of traps baited with the free aldehyde and with the bisulphite-adduct of the pheromone.

The bisulphite adduct of (Z)-9-hexadecenal was prepared according to the same procedure described in Example 1, and preliminary test for the regeneration of the aldehyde from its bisulphite adduct, carried out according to the procedure of Example 2, gave satisfactory results.

Nine polyethylene phials with a capacity of about 2 ml and a suitable polyethylene plug were charged as follows:

Phials No. $A_1$, $A_2$ and $A_3$ with 7.1 mg of bisulphite adduct of (Z)-9-hexadecenal (corresponding to 5 mg of aldehyde) and a buffer solution at pH 3.7.

Phials No. $B_1$, $B_2$ and $B_3$ with 7.1 mg of bisulphite adduct of (Z)-9-hexadecenal (corresponding to 5 mg of aldehyde) and a buffer solution at pH 6.9.

Phials No. $C_1$, $C_2$ and $C_3$ with 5 mg of free (Z)-9-hexadecenal as a control.

Each one of the nine phials was used to bait a suitably adhesive-coated trap (the traps commercialized by Montedison S.p.A. with the name "Traptest" were used) and the traps were randomly placed in a 2 hectare peach-ochard naturally infested by E. candidula. At time intervals the number of males of E. candidula caught in the traps was counted and, when necessary, the adhesive walls were replaced by fresh ones.

The results expressed as number of males caught by the traps at each time interval are reported on the following Table 6.

TABLE 6

| Time intervals (days)[a] | Number of males of E. candidula caught on traps | | |
|---|---|---|---|
| | $A_1 + A_2 + A_3$ | $B_1 + B_2 + B_3$ | $C_1 + C_2 + C_3$ (control) |
| 6[b] | 87 | 111 | 105 |
| 8 | 90 | 84 | 78 |
| 5 | 45 | 66 | 66 |
| 7 | 12 | 15 | 12 |
| 7 | 36 | 39 | 30 |
| 11 | 21 | 12 | 6 |
| 3 | 45 | 15 | 6 |
| 6 | 27 | 30 | 6 |
| 7 | 18 | 12 | 3 |
| Total: 60 days | 381 | 384 | 312 |

Notes to Table 6
[a]days from a count to the successive,
[b]days from the placing of the traps, carried out on July 7, 1981.

The test was ended a few days after the period reported on Table 6 since no infestation could be observed.

The baits of traps $A_1$ to $A_3$ and $B_1$ to $B_3$ were then analyzed and about 50% of the theoretical starting aldehyde (5 mg) was recovered from the remaining bisulphite adduct.

The results reported on Table 6 show how the traps baited with the bisulphite adduct of (Z)-9-hexadecenal and the buffer solution, according to the invention, release the pheromone by a homogeneous and constant *trend, over at least 60 days.*

The traps baited only with (Z)-9-hexadecenal ($C_1$ to $C_3$) are scarcely effective after about 30–35 days.

This is in agreement with the fact that normal baits for the capture of E. candidula are usually monthly replaced by fresh baits.

What we claim is:

1. A slow release formulation of pheromones consisting of aldehydes, comprising bisulphite adducts of the aldehydes and a buffer solution having a pH value ranging from 2 to 10.

2. A slow release formulation of pheromones consisting of aldehydes according to claim 1, containing a buffer solution having a pH value ranging from 3.5 to 8.

3. A method of fighting insects the sex pheromone of which consists of aldehydes, the method consisting in catching and optionally killing the males of the insect species in a trap containing a pheromone source, characterized in that the aldehyde pheromone source consists of a formulation as claimed in claim 1.

4. A trap for insects the sex pheromone of which consists of aldehydes, the trap containing, as a pheromone source, a formulation as claimed in claim 1.

5. A method of disturbing and preventing the copulation of insects the sex pheromone of which consists of aldehydes, consisting in permeating the air in the infested area with the pheromone, characterized in that the source of aldehyde pheromone consists of a formulation as claimed in claim 1.

6. A slow release formulation of pheromones as claimed in claim 1 or 2, containing the bisulphite adduct of the aldehyde (Z)-11-hexadecenal and a buffer solution having a pH value ranging from 3.5 to 8.

7. A method as claimed in claim 3 used in the fight against insects belonging to species *Heliothis armigera* by means of a formulation according to claim 6.

8. A method as claimed in claim 5 used in the fight against insects belonging to species *Heliothis armigera* by means of a formulation according to claim 6.

9. A method as claimed in claim 7 used in the defence of cotton cultures from insects belonging to species *Heliothis armigera*.

10. A method as claimed in claim 8 used in the defence of cotton cultures from insects belonging to species *Heliothis armigera*.

11. The bisulphite adduct of (Z)-11-hexadecenal, of formula:

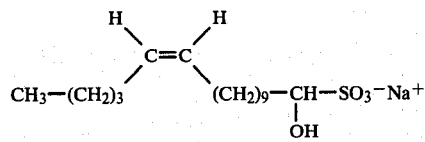

12. A slow release formulation of pheromones as claimed in claim 1 or 2, containing the bisulphite adduct of (Z)-9-hexadecenal and a buffer solution having a pH value ranging from 3.5 to 8.

13. A method as claimed in claim 3 or 5 used in the fight against insects belonging to species *Eustrotia candidula* by means of a composition according to claim 12.

14. The bisulphite adduct of the aldehyde (Z)-9-hexadecenal.

* * * * *